United States Patent [19]
Reilly

[11] Patent Number: 5,687,606
[45] Date of Patent: Nov. 18, 1997

[54] MOISTURE DETECTOR

[75] Inventor: Sean Kevin Reilly, Antioch, Calif.

[73] Assignee: Boart Longyear Company, Martinex, Calif.

[21] Appl. No.: 582,697

[22] Filed: Jan. 4, 1996

[51] Int. Cl.$^6$ .............................. G01M 3/04; G01T 5/10; G01N 22/04
[52] U.S. Cl. .................. 73/73; 73/40.5 R; 73/40.7
[58] Field of Search ........................ 73/73, 40.7, 40, 73/40.5 R

[56] References Cited

U.S. PATENT DOCUMENTS

| | | | |
|---|---|---|---|
| 3,771,349 | 11/1973 | Yatabe | 73/29 |
| 3,786,675 | 1/1974 | Delatorre et al. | 73/27 R |
| 3,954,002 | 5/1976 | Grieser et al. | 73/1 R |
| 4,020,417 | 4/1977 | Brehob et al. | 324/65 R |
| 4,044,607 | 8/1977 | Deal | 73/73 |
| 4,655,076 | 4/1987 | Weihe et al. | 73/73 |
| 4,845,978 | 7/1989 | Whitford | 73/73 |
| 4,991,915 | 2/1991 | Thompson et al. | 324/640 |
| 5,089,895 | 2/1992 | Fraker et al. | 358/229 |
| 5,483,063 | 1/1996 | Hall, Jr. et al. | 250/269.4 |

*Primary Examiner*—Hezron E. Williams
*Assistant Examiner*—J. David Wiggins
*Attorney, Agent, or Firm*—Banner & Witcoff, Ltd.

[57] ABSTRACT

A moisture testing device having various applications including the testing of moisture in the thermal insulation of insulated pipe, the device having a readout and related components connected to a detector assembly which is pivotally mounted at the end of an adjustable pole. The detector assembly utilizes the principle of neutron back scatter or neutron moderation which is known for measuring water and hydrogen, but it is designed as a highly efficient screening device which can for example test thousands of feet of pipe in a day.

22 Claims, 7 Drawing Sheets

MOISTURE DETECTOR

BACKGROUND OF THE INVENTION

The present invention relates to a moisture detector which is mounted on an adjustable pole and can be used to test hard to reach areas and can test from any angle. There are several potential applications for the moisture detector of the present invention, but one particular application is for detecting trapped water in the thermal insulation of pipes and containment vessels without need to remove the insulation.

Water can enter the outer jacketing on a pipe through seams and breaks, and water then becomes trapped against the pipe. Such water will corrode the outside of the pipe, eventually causing a leak, and since this occurs between the pipe and the insulation, it cannot be seen by visual inspection. By way of example, many chemical plant processes require transferring liquid, gases and slurries through pipes at high temperature. Such pipes are thermally insulated to maintain the desired temperature.

Insulated pipes can be inspected for corrosion by stripping off the insulation, but that is a slow and labor intensive procedure and often results in needless destruction of the insulation. Also, some pipes are insulated with asbestos which is extremely expensive to remove and dispose of.

A second option is to use a known device which is capable of detecting corrosion on the pipe without removing the insulation. However, this option is also slow and expensive, and it requires an operator to be in contact with the pipe itself.

The present invention does not make a direct measurement of corrosion, but rather detects moisture which will cause such corrosion. By locating wet areas under the insulation, one can locate the areas most likely to have corrosion. An important advantage of the moisture detector of the present invention is that it can test thousands of feet of pipe in a day. An operator can then use the collected data on moisture to target wet areas and then either strip the pipe to inspect it or use the known corrosion technique to evaluate any damage.

The moisture detector of the present invention has been used successfully to test pipe and vessel insulation for water intrusion. It has also been used to detect the level of tanks which store hydrogenous material. Many other applications are possible including roof moisture surveying, measuring water content of walls to evaluate water damage in buildings, and measuring the water content of horse race tracks to indicate the moisture in the track which affects racing conditions.

It is known in the art to measure moisture in soil using a CPN Hydroprobe which is a device sold by the assignee of the present invention. Such a device includes a housing with extensive measuring apparatus, and a cylindrical member which is connected to the remaining apparatus and which can be inserted into holes drilled in the ground.

It is also known to mount four such CPN hydroprobes on a carriage which travels along a length of insulated pipe and is stopped periodically to take moisture measurements at different quadrants around a selected section of pipe. Thus, using four such Hydroprobes mounted on one carriage, as the carriage is rolled along the pipe, measurements can be taken in each of the four quadrants, and in that manner an operator can determine where any moisture is trapped in the insulation. However, the foregoing moisture detector is generally limited to use on straight runs of pipe. For example, it would be impractical to use such a device in a refinery due to the bends and obstructions in such pipe.

The moisture detector of the present invention is preferably used to measure moisture from one side of a pipe only, which allows an operator to easily go around support structures, branch lines, and other obstructions which would require disassembly and removal of the prior known device described above. I have also found that the bottom of a pipe on a cross section is the wettest, so I do not believe it is necessary to measure moisture at four different quadrants around the circumference of a pipe.

The technology for making the moisture measurement with the present invention involves the principle of neutron backscatter or neutron moderation which is a known principle for measuring water and hydrogen. The isotope Americium 241/Beryllium is used in a sealed source form, and emits fast neutrons from the center of the source detector assembly. The neutrons travel out from the source in all directions. In accordance with the present invention, the source is very close to the material being tested, so many neutrons travel into the material under test. The neutrons are similar in mass to hydrogen atoms, and when they collide with hydrogen, they lose energy and slow down. Collisions with hydrogen also alter their direction as they slow down, and some slow or thermal neutrons make their way back to the detectors which are a component of the moisture detector.

The present invention utilizes two thermal neutron detectors. By way of example, one acceptable type of detector is an $He^3$ detector comprising a pulse ionizing chamber filled with $helium^3$ gas. A thin wire mounted in the center of such a detector is connected to a DC voltage. A center wire or anode will produce a small negative charge as the $He^3$ gas ionizes when a thermal neutron collides with it. The charge is then converted to a voltage pulse and amplified by a power amplifier circuit.

The invention preferably uses two detector tubes, and the pulse from the detector corresponds to a thermal neutron collision with the $He^3$ gas inside one of the two detector tubes. The pulse is amplified and travels from the detector assembly to a micro controller assembly in a readout through cables which are provided or through any appropriate electrical connection. The number of pulses occurring in a given period of time is proportional to the amount of hydrogen near the detector assembly.

The micro controller in the readout assembly will turn on the detectors by applying the necessary dc voltage, and the controller will then start an internal timer so as to accumulate pulses for a given time period. During such a count, a readout display will indicate "counting," and an indicator on a start/enter switch will be illuminated. When the count is completed, the counting indicator will turn off and the controller will display the count which is proportional to the water content. Typical count times take from one to 64 seconds and are operator-selected. The precision of the test increases with the time of the test.

Because the moisture detector of the present invention measures hydrogen rather than water, any material containing hydrogen will increase the count rate. The reading can be influenced by the contents of the pipe, the jacketing material covering the insulation, or the type of insulation itself. The distance from the contents of the pipe will also vary the degree of influence the contents have on the data. All such variables can make a direct moisture reading difficult.

Directly reading a moisture percent would require a calibration for every pipe configuration. While the user may do that, it is much easier to take a relative measurement. By taking several quick tests on the pipe, an operator can establish a baseline of what he considers dry. Such a baseline can be taken on the top of the pipe or at areas which are suspected to be dry. A new baseline must be established each time the pipe configuration or vessel changes.

The foregoing technology concerning the actual measurement of hydrogen through use of the principle of neutron back scatter or neutron moderation for measuring hydrogen or water is generally known. However, it is an object of the present invention to provide a moisture detector configured for use on a pole; preferably an adjustable pole, so it can test hard-to-reach areas and can test from any angle.

Another of my objects is to provide a moisture detector which is safer for the operator as compared to the prior use of four CPN hydroprobes on a carriage, since the present invention utilizes a single source and permits a greater distance between the source and the operator.

A further object of my invention is to provide a moisture detector which can be held against a pipe or other object being measured so it can easily move around obstructions and is not limited to use on long, straight runs of pipe.

Another of my objects is to provide a moisture detector which allows an operator to test locations up to approximately ten or more feet away and which can measure a flat or curved surface from the top, side or bottom.

The foregoing and other objects and advantages of my invention will be apparent from the following description of a preferred embodiment thereof, taken in conjunction with the accompanying drawings.

Now, in order to acquaint those skilled in the art with the manner of making and using my invention, I shall describe, in conjunction with the accompanying drawings, a preferred embodiment of the invention.

DETAILED DESCRIPTION OF THE INVENTION

Figure 1:
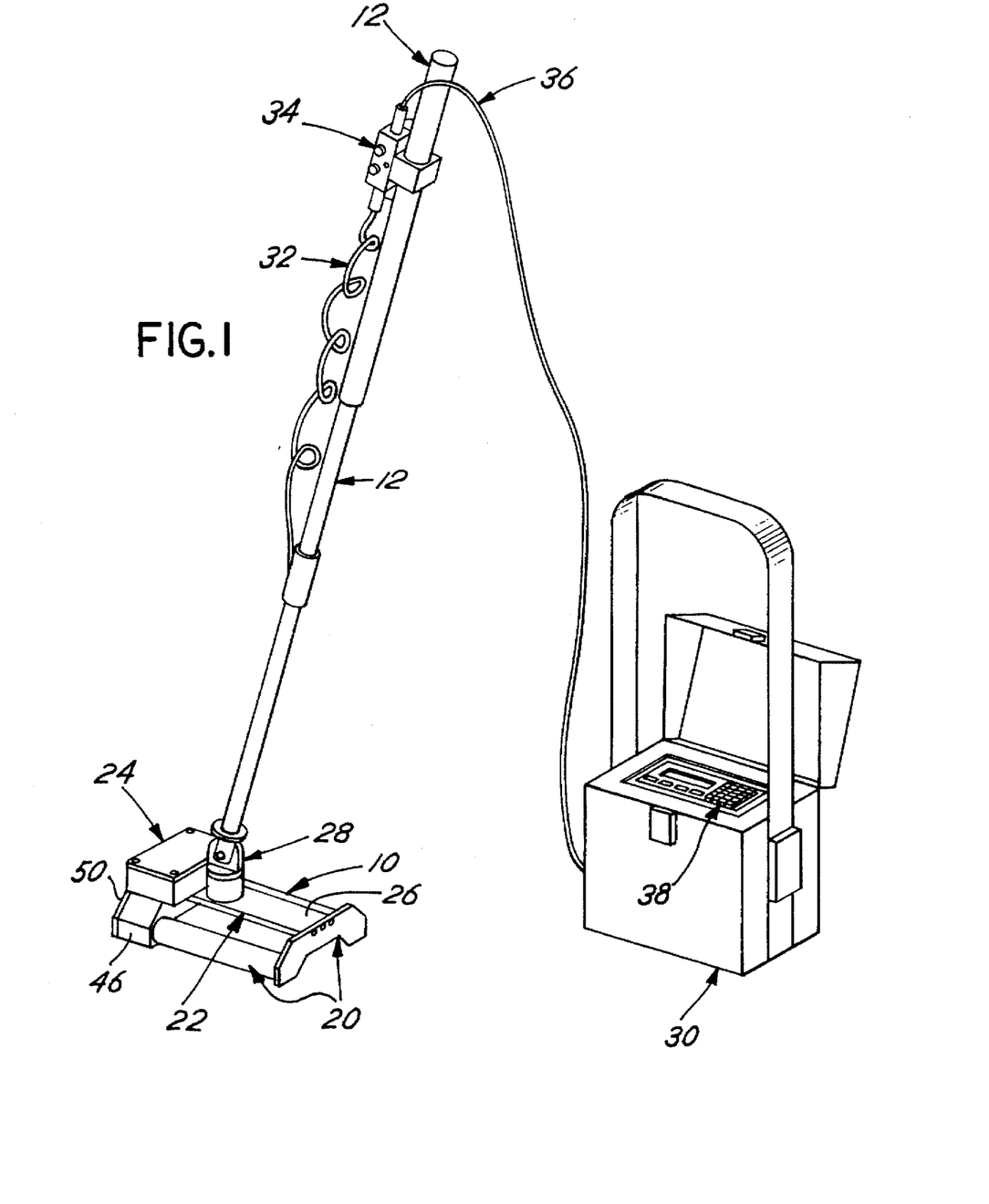
FIG. 1 is a perspective view of the moisture detector of the present invention.
Figure 2:
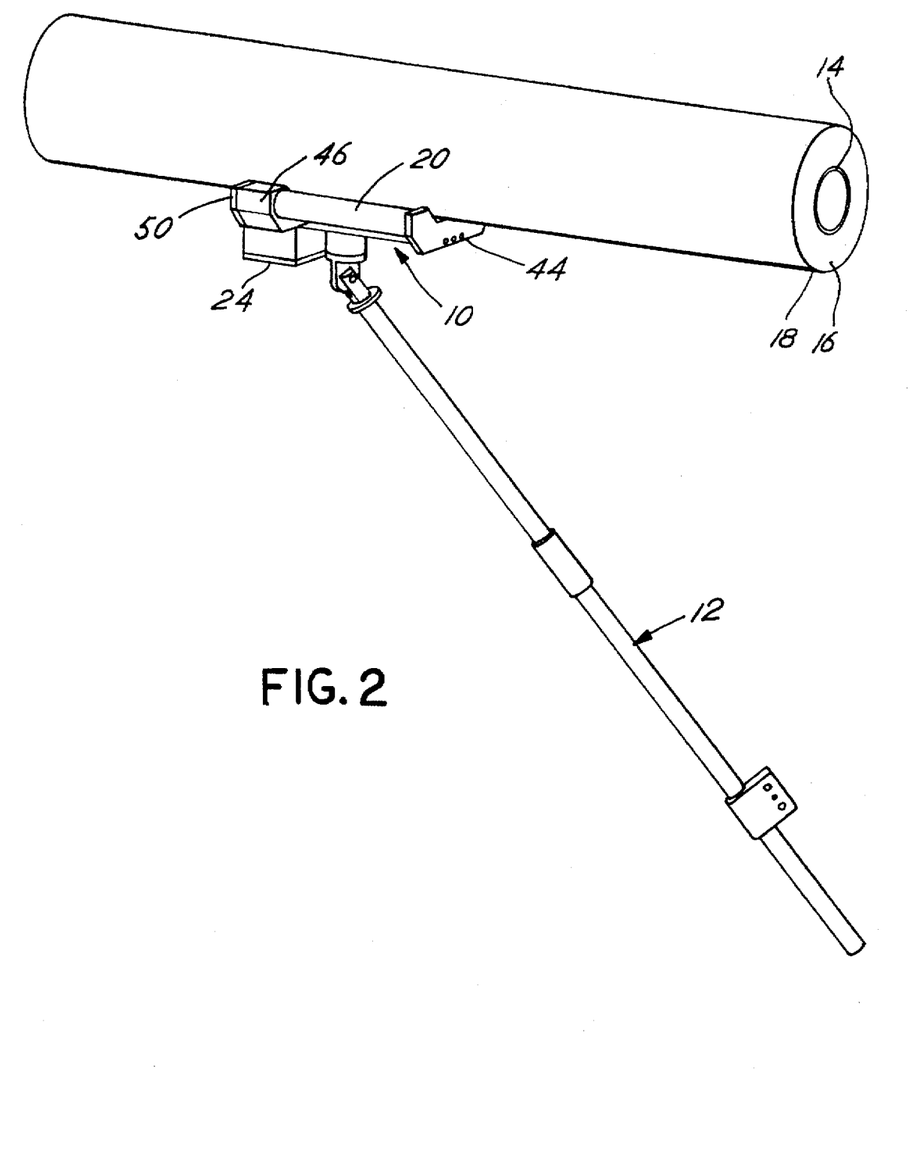
FIG. 2 is a perspective view showing the detector assembly portion of the moisture detector mounted on an end of an adjustable pole and held against the bottom surface of an insulated pipe for measuring moisture in the pipe.

FIG. 1 shows a detector assembly 10 mounted on the lower end of an adjustable pole 12. As shown in FIG. 1, the detector assembly 10 is generally C-shaped as it faces downwardly to permit it to be held against the surface of a length of insulated pipe for detecting moisture beneath the insulation. If the detector assembly were designed for use with a single diameter of pipe, it could be made arcuate to fit more closely to the contour of the pipe. However, by making the detector assembly with a generally C-shaped contour, it can be held in a fixed and stable position against the underside of a length of pipe and can be used with pipes of varying diameters. FIG. 2 shows the detector assembly 10 being held against the underside of a length of insulated pipe, the pipe being shown at 14 covered by insulation 16 and an outer jacket 18.

Still referring to FIG. 1, thermal neutron detectors which may be helium$^3$ detector tubes are shown generally at 20, and the center of the detector assembly which is the source location is shown at 22. A high voltage power supply and amplifier circuit is shown at 24, and a swivel connection by which the lower end of the tube 12 is connected to a top plate 26 of the detector assembly is shown generally at 28. The foregoing components of the moisture detector of the present invention are all carried on the end of the pole 12 so an operator can hold the detector assembly 10 against an insulated pipe or other object as shown in FIG. 2.

FIG. 1 also shows the other components of the moisture detector which are separate from the detector assembly and may be carried in a shoulder bag 30 by an operator. Such other components include a start/enter flex cable 32, a start/enter switch assembly 34 mounted near the upper end of the pole 12, a readout assembly cable 36, and a readout assembly 38.

Figure 6:
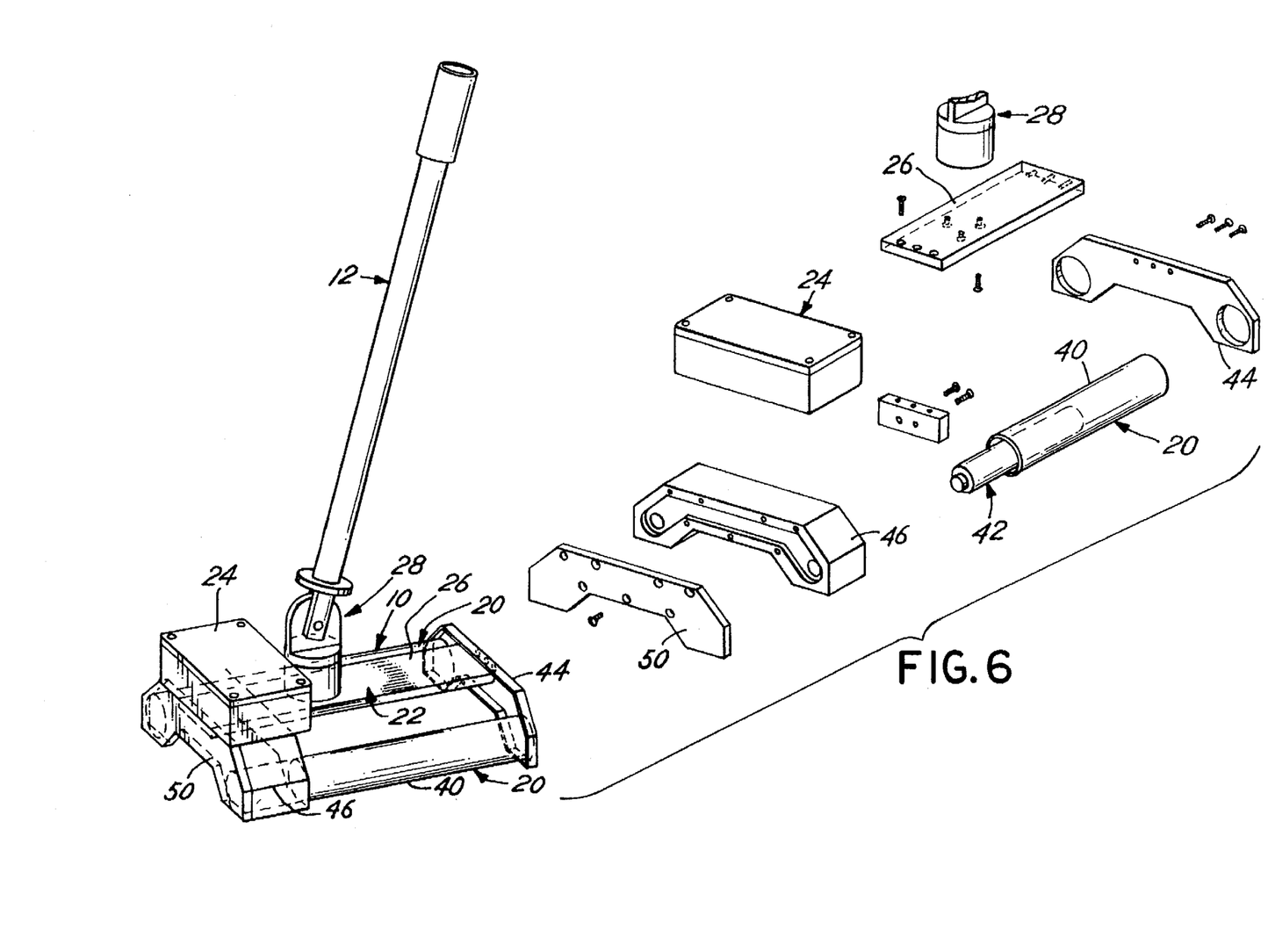
FIG. 6 is an exploded perspective view showing a detector assembly mounted at the lower end of an adjustable pole and showing the various components which comprise the detector assembly that is carried at the end of the pole including a pair of detector tubes mounted inside of shield tubes.

Reference is now made to FIG. 6 which illustrates the components which comprise the C-shaped detector assembly 10. The active components are a pair of detector tubes 20 which comprise tube shields 40 and He$^3$ detector tubes 42 positioned inside the shields. As shown in the lower left-hand portion of FIG. 6, the right-hand ends of the tube shields 40 are received in openings in an end block 44, and the left-hand ends of the tube shields 40 are received in openings in an end plate 46, so that the two detector tubes 20 are arranged in parallel relation. A block plate 50 is mounted on the outside of the end plate 46 at the opposite end of the end block 44.

The top plate 26 extends longitudinally and has its right-hand end connected to an upper edge of the end block 44 and its left-hand end connected along the upper edge of the block plate 50. The detector box assembly 24 is mounted on top of top plate 26 at the left-hand end thereof. The swivel connection 28 between the pole 12 and the detector assembly 10 is mounted to the top of the top plate 26.

Other types of structure may be used to construct the detector assembly 10, but in the preferred embodiment there are two detector tubes 20 mounted in parallel relation, the power supply and amplifier circuit 24 are mounted on the detector assembly, a swivel connection 28 is provided between the detector assembly 10 and the lower end of a pole 12, and the underside of the detector assembly (the bottom as viewed in FIG. 6) is generally C-shaped, especially if the detector is intended to measure moisture in insulated pipe. FIG. 6 shows that the profile of the end plate 46, the end block 44, and the block plate 50, are all generally C-shaped. FIG. 2 shows the manner in which those three components all rest on a length of insulated pipe, and the detector tubes 20 are located relative to those components so that the tubes 20 are positioned closely adjacent the outer jacket 18 of the pipe.

Figure 3:
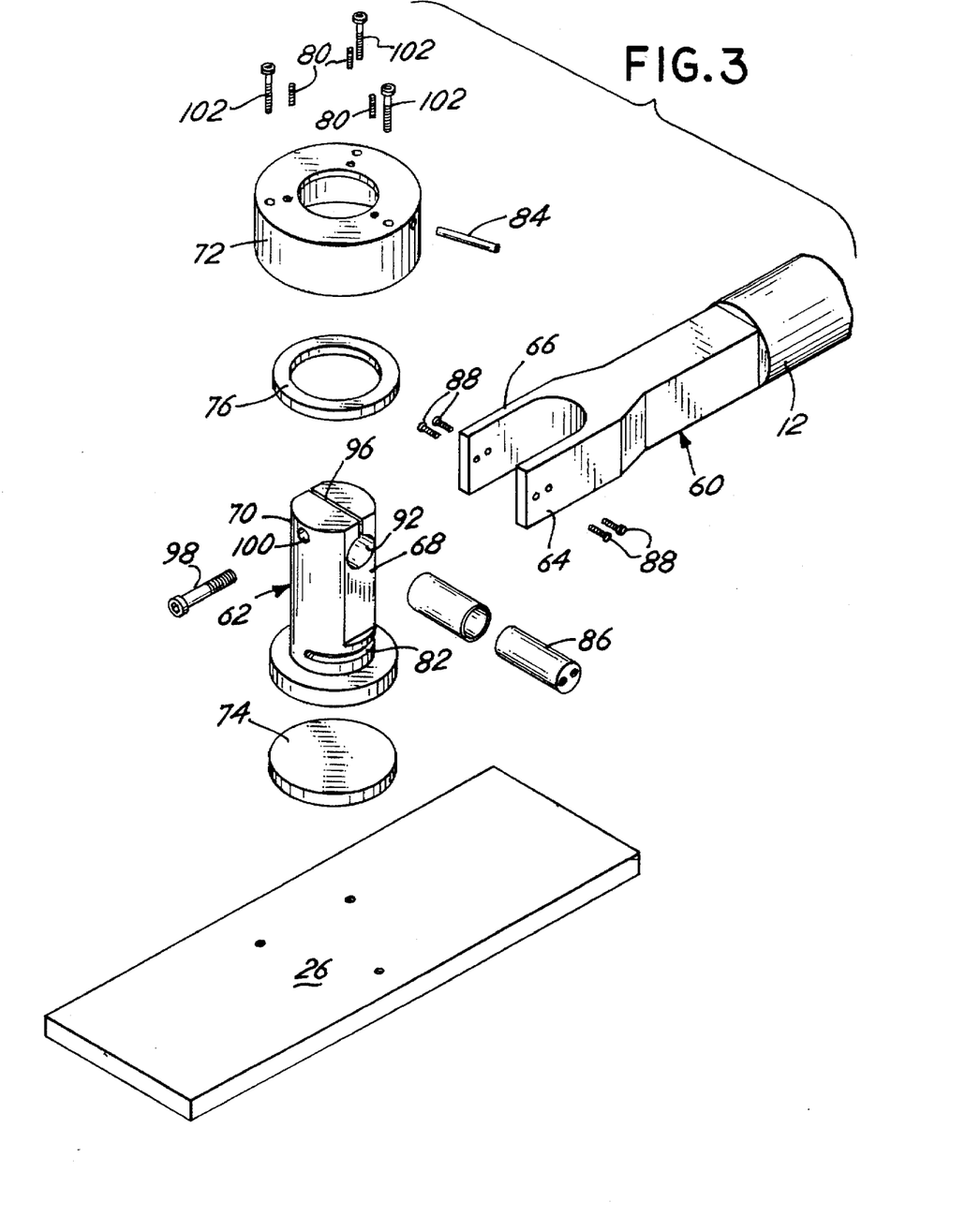
FIG. 3 is an exploded perspective view showing the end of a pole for carrying the detector assembly and showing the various components by which the end of the pole is connected to the detector assembly such that the pole may be moved about two different axes relative to the detector assembly to aid an operator in holding the detector assembly against an object to be tested.
Figure 4:
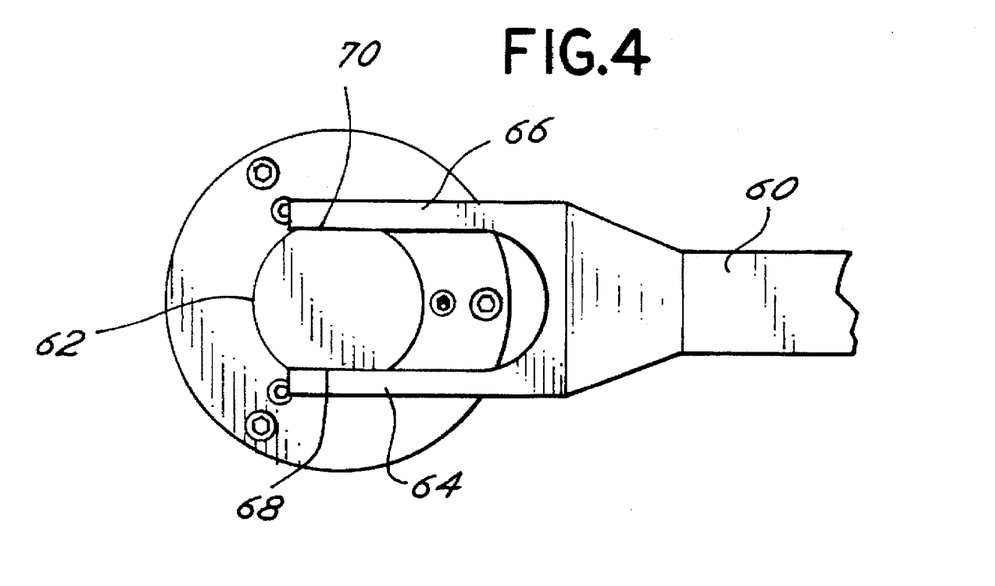
FIG. 4 is a fragmentary top plan view showing the connection between the pole and the detector assembly and indicating how the pole may be rotated 180 degrees about a vertical axis when the detector assembly is positioned in a horizontal plane.
Figure 5:
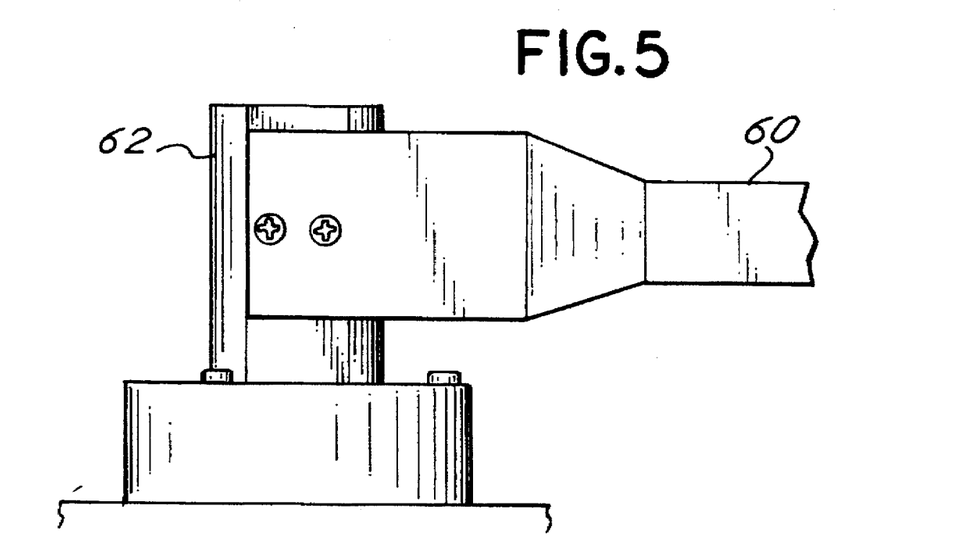
FIG. 5 is a fragmentary side elevational view showing the connection between the pole and the detector assembly and indicating how the pole may be rotated 180 degrees about a horizontal axis when the detector assembly is positioned in a horizontal plane.

Reference is now made to FIGS. 3–5 to describe the swivel connection 28. As previously described, the swivel connection 28 serves to connect the lower end of the pole 12 with the detector assembly 10 by attachment to the top plate 26 of the detector assembly. The swivel or pivot assembly allows the detector assembly 10 to rotate about two perpendicular axes relative to the pole 12. Such rotation is preferably limited to 180 degrees about each of the axes to prevent damage to the attached cable. The pivot also allows the user to vary the friction of movement about each axis.

In describing the pivot assembly, the terms "horizontal" and "vertical" will be used with reference to the top view of FIG. 4 and the side elevation of FIG. 5. A yoke assembly 60 is mounted as an extension at the lower end of pole 12. Movement about the vertical axis is accomplished by moving the yoke assembly 60 which will turn a pivot 62 about its vertical axis. As shown in FIGS. 3–5, the yoke has two flat arms 64 and 66 which closely straddle flat sides 68 and 70 of the pivot 62 so the yoke and pivot will move conjointly about the vertical axis of pivot 62.

The pivot 62 travels inside a pivot cover 72. When the pivot is assembled and attached to the top plate 26 of the detector assembly 10, the pivot 62 rests on a Delrin disk 74 which is positioned on the top plate 26. Above the lip of the pivot 62, a Delrin washer 76 is positioned, and thus the disk 74 and washer 76 act as wear surfaces as the pivot 62 is rotated about a vertical axis. Set screws 80 can be adjusted to vary the pressure on the washer 76 which in turn varies the friction against movement of pivot 62 about its vertical axis. A slot 82 which extends 180 degrees circumferentially around the lower end of pivot 62 will, when assembled, cooperate with a roll pin 84 which is fixed in a hole in the side of the pivot cover 72 so as to limit rotation of the pivot 62 about its vertical axis to 180 degrees.

Movement of the handle about a horizontal axis is accomplished by moving the yoke assembly 60 to turn an axle 86 which is held in the yoke by four screws 88 so the yoke and axle rotate conjointly about the axis of the axle. The axle 86 is positioned inside a nylon sleeve 90 which is positioned in a horizontal hole 92 formed in pivot 62. Thus, the nylon sleeve 90 acts as a wear surface for the axle 86.

A vertical slot 96 is cut down into the upper end of pivot 62 so the pivot is split above the hole 92. A set screw 98 is threaded into a horizontal hole 100 in the side of the pivot 62, so by adjustment of set screw 98, an operator can adjust the friction by clamping the pivot 62 against the nylon sleeve 90 and axle 86. The pivot cover 72 is held down by three screws 101 which thread down into the detector base 26.

The configuration of the detector assembly 10 comprising the generally C-shaped portion which fits against an object to be tested in an important feature. Many testers present a flat surface, whereas the detector assembly of the present invention will fit in a stable manner about a pipe or other curved surface as shown in FIG. 2. Also, the pole 12 is preferably extendable so the operator can adjust the length and thereby permit the operator to keep a maximum distance from the source, which is an added safety feature. The components of the detector assembly 10 are preferably made of metal, e.g., aluminum. Also, the fact that the detector head can pivot about two perpendicular axes relative to the pole facilitates use of the detector in various applications.

Figure 7:
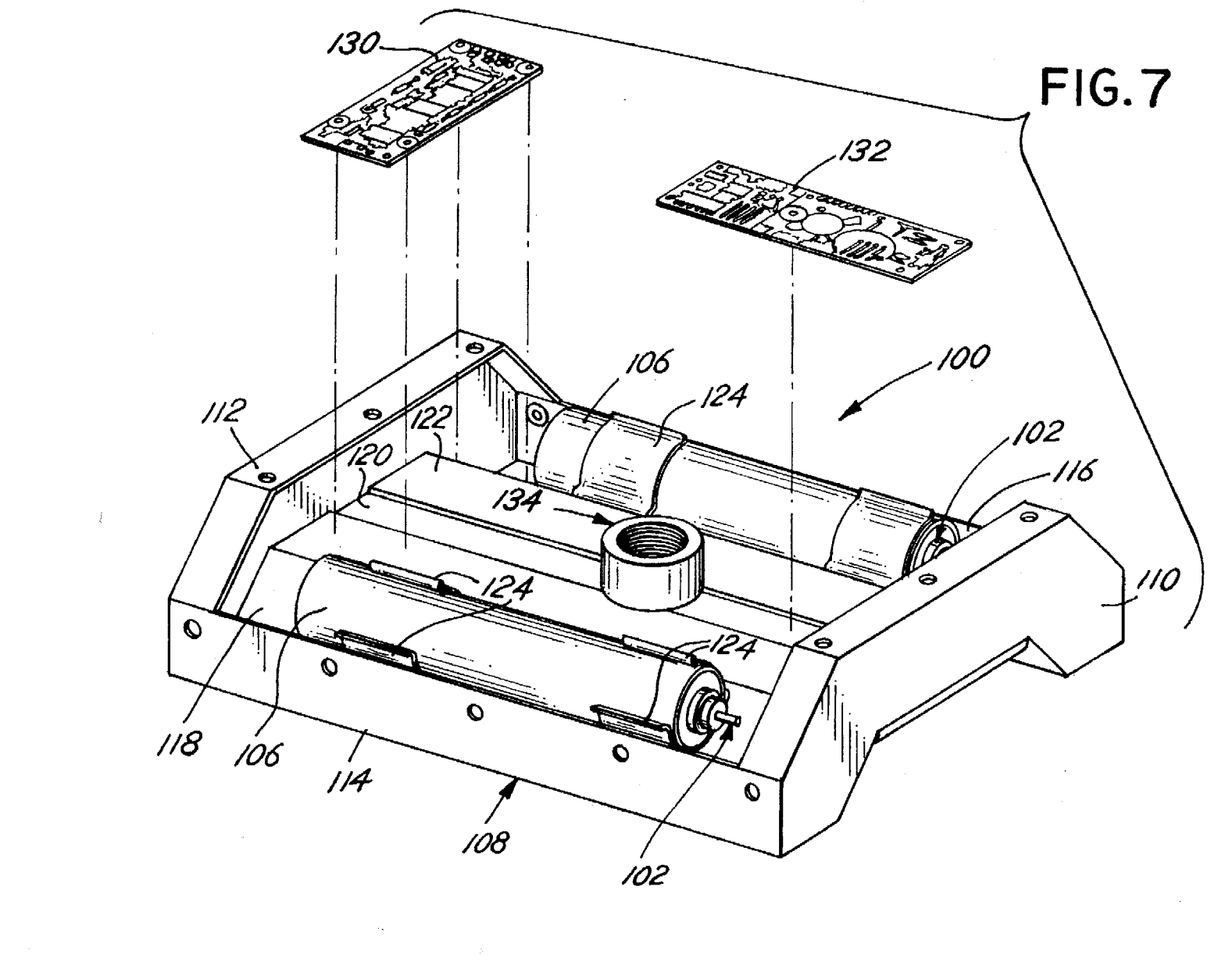
FIG. 7 is an exploded perspective view showing an alternative embodiment of a detector assembly with an alternative type of housing.
Figure 8:
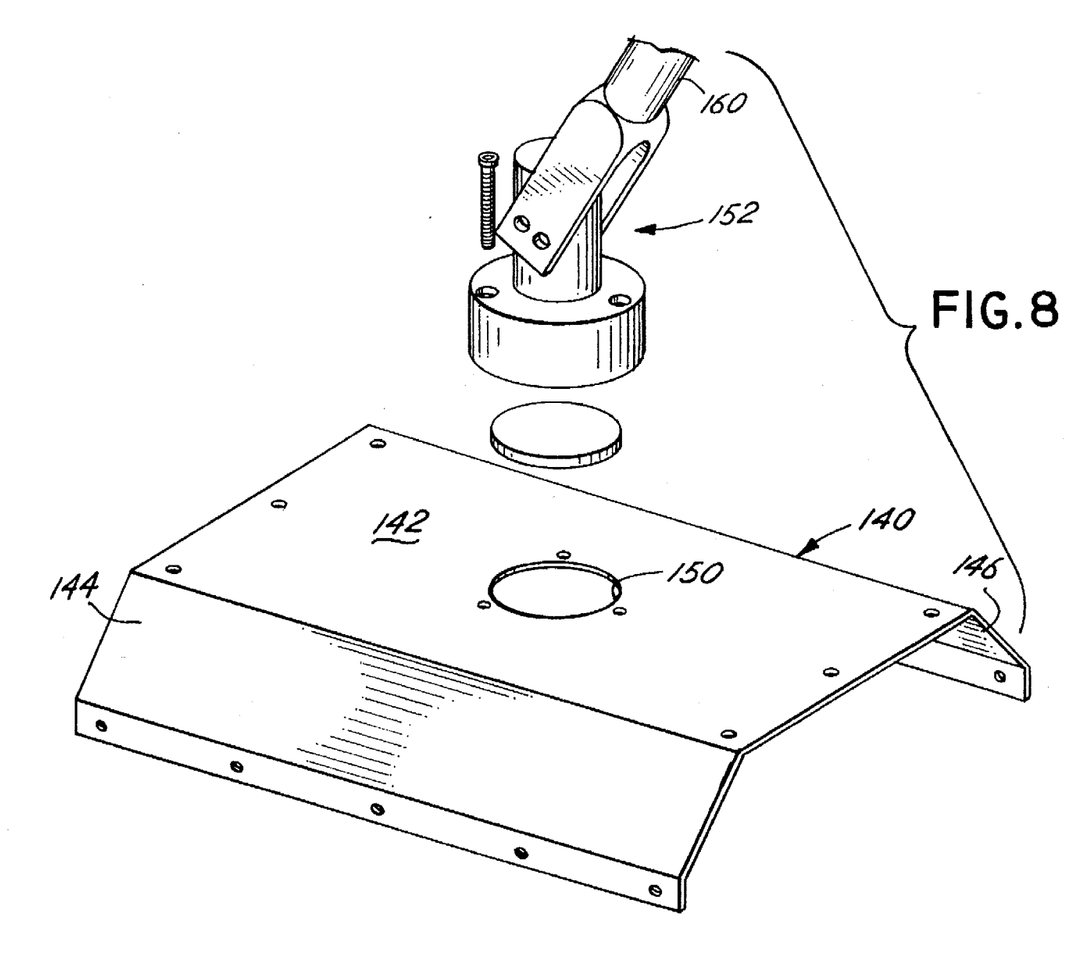
FIG. 8 is an exploded perspective view showing a cover for the housing of FIG. 7 together with structure for connecting the end of an adjustable pole to the detector assembly.

Reference is now made to FIGS. 7 and 8 which show an alternative embodiment of the detector assembly shown in FIG. 6. FIG. 7 shows a detector assembly 100. The assembly 100 includes a pair of thermal neutron detectors 102 which in the embodiment being described may comprise $He^3$ detector tubes positioned inside tubular shields 106.

A housing 108 includes a pair of housing end portions 110 and 112 connected by a pair of longitudinal side frame portions 114 and 116 to create a rigid housing assembly. In addition, bottom wall plates 118, 120 and 122 extend between the end portions 110 and 112 and form a completely enclosed bottom wall beneath the detectors 102.

Each of the detectors 102 is held in position in parallel relation to one another by dips 124 mounted from bottom wall portions of the housing. FIG. 7 further shows a charge preamplifier 130 and a high voltage power supply 132 which mount inside the housing 108. A neutron source is shown at 134.

FIG. 8 shows a cover 140 having a top wall 142 and opposed inclined wall portions 144 and 146. The cover 140 is mounted by screws or other suitable fastening means to the top of the detector assembly 100 of FIG. 7. A round opening 150 is provided in the cover to accommodate swivel mechanism 152 which connects the lower end of a pole 160 to the detector assembly 100 to permit rotation of the detector assembly about two perpendicular axes relative to the pole as previously described.

The detector assembly 100 functions in essentially the same manner as the detector assembly shown in FIG. 6, and it is generally C-shaped at its lower or outer end for the reasons previously described. However, the housing shown in FIGS. 7 and 8 is enclosed both on the top and the bottom as contrasted with the housing of FIG. 6.

In operation, where the application is the moisture testing of insulated pipe, pipe configurations vary greatly, and differences in insulation types, inner and outer diameters, and the effect of the contents, are all factors affecting the measurement. As a result, absolute moisture measurements are difficult to establish, considering the number of variables. A relative measurement may be more appropriate. A reference count taken on a pipe in a suspected dry location, or several different locations, can establish a baseline for the pipe configuration under test.

Typically, the highest levels of moisture in wet insulation are at the lowest point, the bottom side of a horizontal pipe, which means that the top side may be preferable for establishing a baseline. An operator may take test readings at the bottom of a pipe at 1 to 4 second counts every 12 to 18 inches. The counts will fluctuate since radioactive decay is a random event. Suspect areas will have higher counts than other areas. Taking a longer test will help better define the suspect areas. Longer tests also mean increased precision, since the detector can accumulate more data.

All of the tests are normalized, measuring for a 1 second period and then averaging over the period of the test time and then displaying the results as counts per minute. The device can allow user selectable test times of from 1 second to over 900 seconds. However, the results will be normalized to counts per minute. The selected test time will normally be a compromise between precision and speed. Typically, the 1 second or 4 second test time will be adequate for most circumstances.

The device has two basic modes of operation. First is the standard data collection mode where a reading is taken for the selected test time (from 1 to 960 seconds) and displayed on the readout device. At this point, the operator will be able to see the final value in counts per minute and then store that data point if he wishes to do so. The second mode of operation is to allow the user to take continuous "quick test" modes, whereby the unit will take continuous 1 second test samples and compare that value with a calibration value. The automatic computation will allow the device to signal to the user that the data was less than or more than a predetermined threshold. This will allow the user to detect moisture at a much faster (albeit at a less precise) rate.

As previously noted, an important application for the moisture detector of the present invention is for use as a screening device as in the case of testing insulated pipe for moisture. Such device allows an operator to quickly locate areas where high moisture is present. Once such areas are located, more thorough corrosion inspection techniques which have a lower rate of test may be used to check potential problem areas. The detector of the present invention will permit a single operator to test several hundred feet of pipe per hour. The following test rates can be achieved:

| Reading Time | Test Rate |
| --- | --- |
| 960 seconds reading | 1.25 ft/hr* |
| 16 seconds reading | 200 ft/hr* |
| 4 seconds reading | 600 ft/hr* |
| 1 second reading | 1200 ft/hr* |
| "quick test" reading | 2700 ft/hr** |

*Includes 2 seconds between readings
**In "quick test" the readings are continuous with less than 1 second between readings.

It will be understood that the cable connecting the detector assembly 10 in FIGS. 1, 2, and 6 or 100 in FIG. 7 to the readout shown at 38 in FIG. 1 may be replaced by other known electrical connections which can transmit data from the detector to the readout. Thus, the invention is not limited to the use of cable for such purpose.

I claim:

1. A mobile and portable moisture detector comprising, in combination, a readout assembly, a detector assembly, said detector assembly having a non-flat surface for engagement with an object to be tested, electrical means connecting said detector assembly to said readout assembly, and said detector assembly being pivotally mounted on an end of a pole so an operator using said pole can hold said non-flat surface against an object to be tested, wherein said non-flat surface is generally C-shaped or shaped with an arcuate contour.

2. A moisture detector as defined in claim 1 where said detector assembly is connected to said end of said pole by a swivel assembly which permits said detector assembly to pivot about two different axes relative to the axis of said pole.

3. A moisture detector as defined in claim 1 where said electrical means connects said detector assembly to said readout assembly through a switch assembly.

4. A moisture detector as defined in claim 1 where said detector assembly includes a pair of tubularly-shaped thermal neutron detectors mounted parallel to one another and arranged to be held adjacent to an object to be tested when said non-flat surface is held against said object to be tested.

5. A moisture detector as defined in claim 1 where said detector assembly operates on the principle of neutron backscatter to measure hydrogen.

6. A moisture detector as defined in claim 1 where said detector assembly includes a high voltage power supply and amplifier circuit.

7. A moisture detector as defined in claim 1 where said pole is adjustable in length and permits an operator to be as much as ten feet or more away from an object being tested.

8. A moisture detector as defined in claim 1 where said readout assembly is located in a shoulder bag intended to be worn by an operator who holds said detector assembly against an object to be tested through use of said pole.

9. A moisture detector as defined in claim 1 where a start/enter switch is mounted near an upper end of said pole for actuation by an operator holding said pole.

10. A moisture detector comprising, a readout assembly, a detector assembly, said detector assembly having a non-flat surface for engagement with an object to be tested, wherein said non-flat surface is generally C-shaped or shaped with an arcuate contour, electrical means connecting said detector assembly to said readout assembly, said detector assembly being mounted on an end of a pole by a swivel assembly so an operator using said pole can hold said non-flat surface against an object to be tested, said swivel assembly permitting said detector assembly to pivot about two different axes relative to said pole, said detector assembly being operated on the principle of neutron backscatter to measure hydrogen, said detector assembly including a pair of tubularly-shaped thermal neutron detectors mounted parallel to one another and arranged to be held adjacent to an object to be tested when said non-flat surface is held against said object to be tested, and said detector assembly including a high voltage power supply and amplifier circuit.

11. A moisture detector as defined in claim 10 where said electrical means connects said detector assembly to said readout assembly through a switch assembly.

12. A moisture detector as defined in claim 10 where said pole is adjustable in length and permits an operator to be as much as ten feet or more away from an object being tested.

13. A moisture detector as defined in claim 10 where said readout assembly is located in a shoulder bag intended to be worn by an operator who holds said detector assembly against an object to be tested through use of said pole.

14. A moisture detector as defined in claim 10 where a start/enter switch is mounted near an upper end of said pole for actuation by an operator holding said pole.

15. A method of testing moisture in an object comprising the steps of hold a detector assembly against the object to be tested through use of a pole, the detector assembly being pivotally mounted on an end of said pole, said detector assembly being of the type which measures hydrogen based on the principle of neutron backscatter and including at least one thermal neutron detector and conducting signals from said detector assembly through electrical means to a readout assembly which is located separately and is not mounted on said pole, said detector assembly further including a generally C-shaped surface which is held against said insulated pipe.

16. A method as defined in claim 15 where two of said detectors are used.

17. A method as defined in claim 15 where an operator uses a switch mounted near an upper end of said pole to connect said detector assembly to said readout assembly.

18. A method as defined in claim 15 where an operator carries said readout assembly in a shoulder bag while using said pole to carry said detector assembly.

19. A method as defined in claim 15 where a power supply and amplifier are mounted in a compact electronics module adjacent said detector assembly.

20. A method as defined in claim 15 where said pole is adjustable in length so an operator can control the distance between the object being tested and the operator.

21. A method of testing moisture in a length of insulated pipe comprising the steps of holding a detector assembly against insulated pipe to be tested through use of a pole where said detector assembly includes a generally C-shaped surface or arcuate contoured surface which is held against said insulated pipe, said detector assembly being pivotally mounted on an end of said pole, said detector assembly being of the type which measures hydrogen based on the principle of neutron backscatter and including at least one thermal neutron detector, and conducting signals from said detector assembly through electrical means to a readout assembly which is located separately and is not mounted on said pole.

22. A method of detecting moisture in a length of insulated pipe comprising the steps of holding a detector assembly against insulated pipe to be tested through use of a pole, said detector assembly being mounted on an end of said pole by a swivel assembly which permits pivoting about two different axes, said detector assembly being of the type which measures hydrogen based on the principle of neutron back scatter and including a pair of thermal neutron detectors, conducting signals through electrical means from said detector assembly to a readout assembly which is carried by an operator separately and is not mounted on said pole, and said detector assembly including a generally C-shaped surface or arcuate contoured surface which is held against insulated pipe to be tested.

* * * * *